United States Patent [19]
Chen et al.

[11] Patent Number: 5,957,960
[45] Date of Patent: Sep. 28, 1999

[54] INTERNAL TWO PHOTON EXCITATION DEVICE FOR DELIVERY OF PDT TO DIFFUSE ABNORMAL CELLS

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 08/850,909

[22] Filed: May 5, 1997

[51] Int. Cl.⁶ ..................................................... A61N 5/06
[52] U.S. Cl. .................................. 607/92; 607/88; 607/89
[58] Field of Search ............................. 607/88–92; 606/2, 606/3, 9, 10, 13; 604/19–21

[56] References Cited

U.S. PATENT DOCUMENTS

| | | | |
|---|---|---|---|
| 4,822,335 | 4/1989 | Kawai et al. | 604/20 |
| 5,445,608 | 8/1995 | Chen et al. | 604/20 |
| 5,616,140 | 4/1997 | Prescott | 606/9 |
| 5,707,401 | 1/1998 | Talmore | 607/88 |

OTHER PUBLICATIONS

Denk, Winfried, "Two–Photon Exciation in Functional Biological Imaging," Journal of Biomedical Optics 1(3), pp. 296–304, Jul. 1996.

Smith, G. et al., "Rapid Communication, An Efficient Oxygen Independent Two–Photon Photosensitization Mechanism," Photochemistry and Photobiology, vol. 59, No. 2, pp. 135–139, 1994, © 1994 American Society for Photobiology.

Higgins, Thomas V. (Contributing Editor), "Optoelectronics: the next technological revolution," Laser Focus World, Nov. 1995, 8pp.

"Two–Photon Therapy Holds Promise as Cancer Treatment," Photonics Technology World, Photonics Spectra, Jan. 1997, 2pp.

"Minimally Invasive Laser Surgery," Method developed at the Dept. of Energy's Oak Ridge National Laboratory in Oak Ridge, Tennessee, by Craig Dees, Eric Wachter, Walt Fisher, Gil Brown, and Bill Partridge, 1pg.

Oh, Dennis H., et al., " Research Note, Two–Photon Excitation of 4'-Hydroxymethyl–4,5',8–Trimethylpsoralen," Photochemistry and Photobiology, 1997, 65(1): 91–95.

Hell, Stefan W., et al., "Three–Photon Excitation in Fluorescence Microscopy," Journal of Biomedical Optics, 1(1), 71–74, Jan. 1996.

*Primary Examiner*—Linda C. M. Dvorak
*Assistant Examiner*—Bryan K. Yarnell
*Attorney, Agent, or Firm*—Ronald M. Anderson

[57] ABSTRACT

A plurality of light sources that emit light having a long wavelength are energized for an extended period of time to increase the likelihood of two photon absorption by cells that have preferentially absorbed a photoreactive agent such as psoralen. The cells are preferably microscopic metastatic cancer cells that are diffusely distributed throughout a treatment site, for example, within an organ. The plurality of light sources are arranged in a spaced-apart array, mounted on a support plate that includes a plurality of conductive traces. A plurality of such arrays are preferably mounted to a flexible sheet that can conform to an outer surface of an organ being treated. Because the light emitted by the light sources is in the infrared or near infrared waveband, it penetrates deeply into the tissue at the treatment site. The duration of the treatment and the number of light sources employed for administering the therapy increases the likelihood of two photon absorption by the metastatic cancer cells, which has been shown to activate the photoreactive agent to destroy cancer cells in a tumor, even though the characteristic light absorption waveband of the photoreactive agent is in the ultraviolet waveband.

24 Claims, 3 Drawing Sheets

POWER SUPPLY &
SELECTIVE ARRAY CONTROL

5,957,960

INTERNAL TWO PHOTON EXCITATION DEVICE FOR DELIVERY OF PDT TO DIFFUSE ABNORMAL CELLS

FIELD OF THE INVENTION

The present invention generally relates to an apparatus and method for delivering long wavelength light to administer photodynamic therapy (PDT), and more specifically, applies to administering long wavelength light from an internally implanted array of light sources to destroy diffuse abnormal cells in an organ by causing a photodynamic reaction in a photoreactive agent that has been infused into the organ.

BACKGROUND OF THE INVENTION

Most techniques used to treat cancer (other than chemotherapy) are directed against a defined tumor site in an organ, such as a brain tumor, or a tumor in the breast. When the mass of abnormal cells is consolidated and sufficiently large, either surgical removal, destruction of the tumor mass using either heat or cold, or radiation therapy becomes possible because the target is readily identifiable and localizable. However, it is not uncommon for a cancer that has initially occurred at a primary site to metastasize and spread into adjacent organs as diffuse clusters of abnormal cells. These small clusters of cells, which are more properly referred to as microscopic diffuse metastatic deposits, are not localizable and are virtually impossible to treat other than by chemotherapy. However, because of the diverse nature of cancer cells, only a portion of the metastatic abnormal cells will likely be susceptible to chemotherapy, leaving abnormal cells that are resistant to the therapy to multiply until the patient dies from the concomitant effects of the malignant cells.

This problem can arise, for example, when colorectal cancer occurs in a patient. Although the treatment applied to a cancerous tumor in the colon may be effective to destroy the tumor at that primary site, metastatic cancer cells often spread from this primary site into the liver (and into other organs of the body). Ultimately, because none of the conventional techniques for treating cancer are truly effective in destroying the microscopic metastasized cells, the patient will die when the liver ceases functioning due to the spread of the abnormal cells. Clearly, a new and more effective approach is required to destroy such microscopic diffuse non-localizable metastatic deposits in an organ that cannot be fully destroyed by any conventional treatment.

Recently, a new method for treating breast cancer has been developed by Eric Wachter et al. at Oak Ridge National Laboratory, and this method appears to be useful for treating other types of cancer. The technique employs a Ti:sapphire laser to administer PDT with light in the near infrared, i.e., relatively long, wavelength light. In conventional PDT, a light-activatable photoreactive agent is administered to a treatment site in or on a patient's body and is preferentially absorbed by abnormal cells at the site. When light from a laser or other source having a waveband corresponding to the absorption waveband of the photoreactive agent is applied to the abnormal cells, the photoreactive agent absorbs the light. The resulting photodynamic reaction then destroys the abnormal cells comprising the tumor.

The new technique developed by the Oak Ridge research group differs from conventional PDT in several respects. In contrast to conventional PDT, the near infrared light produced by the Ti:sapphire laser is at a wavelength substantially longer than the characteristic absorption waveband of the photoreactive agent employed. Instead of the single photon absorption process involved in a conventional photodynamic reaction, a two photon process occurs when a pulse of the 700–1000 nm light is focused on the tumor being treated. Due to its relatively long wavelength, the near infrared light emitted by a mode-locked Ti:sapphire laser can penetrate into tissue up to 8 cm. or more, making it possible to pinpoint tumors that are relatively deep within the patient's body, well below the dermal layer. The two photon process is able to activate a photoreactive agent such as psoralen, which is normally activated during PDT by ultraviolet light having a much shorter wavelength. Since light having a shorter wavelength penetrates a shorter distance into tissue, the long wavelength light is preferable. In addition, the longer wavelength light causes less damage to tissue than the shorter wavelength ultraviolet light normally used to activate psoralen.

In a paper entitled "Two-Photon Excitation of 4'-Hydroxymethyl-4,5', 8-Trimethylpsoralen," by Dennis H. Oh et al., *Photochemistry and Photobiology*, 1997, 65(1): 91–95, the magnitude of the emission spectrum of this specific psoralen when excited by two photon absorption is reported to depend quadratically on the intensity of the laser excitation. Based on this article, it appears that to be effective in causing an acceptable level of two photon absorption, a focused, high intensity light source must be used. Thus, it appears that although the technique developed by the Oak Ridge research group is useful in destroying cancer cells well below the surface of the patient's skin, a high power laser is required for producing the near infrared light and the laser must be aimed at a pinpoint location in an organ where a tumor is known to exist. It would therefore appear that this technique is not applicable to destroying diffuse, microscopic metastatic cells that have invaded an organ.

A different approach therefore seems to be required to achieve long wavelength, two photon excitation of an appropriate photoreactive agent to destroy abnormal cells that are randomly dispersed throughout an organ. Instead of using a high power light source, it will likely be possible to use a plurality of lower power light sources and to administer the light therapy for a long period of time. Preferably, if this PDT must be applied for an extended period of time, the patient should remain mobile during the treatment. A Ti:sapphire laser source clearly cannot be used for this purpose due to its expense, and the requirement that the patient remain motionless during the treatment with such a laser.

SUMMARY OF THE INVENTION

In accord with the present invention, an apparatus is defined for administering a photodynamic therapy to a treatment site within a patient's body using light having an infrared or near infrared waveband. The light is intended to destroy microscopic, diffuse metastatic cells at the treatment site that have absorbed a photoreactive agent having a characteristic absorption waveband for light that is substantially shorter than the near infrared waveband. The apparatus includes a support plate on which are disposed a plurality of electrical conductors that are adapted to couple to a source of an electrical current. A plurality of light sources are mounted on the support plate in electrical contact with the plurality of electrical conductors so that the plurality of light sources are energized by an electrical current conveyed by the plurality of electrical conductors. The light sources emit light having a long wavelength that is in the near infrared to infrared waveband. Means are included for directing the light emitted by the plurality of light sources so that the light emitted from one light source crosses the light emitted by a different light source. Use of a plurality of light sources increase the likelihood of two photons substantially simultaneously being absorbed by the photoreactive agent in a microscopic, diffuse metastatic cell at the treatment site. Absorption of two photons by the photoreactive agent results in a photodynamic reaction that destroys the cell.

The apparatus also preferably comprises a plurality of support plates. On each support plate are mounted a plurality of light sources that are energized by current conveyed by a plurality of conductive traces. A flexible sheet is provided on which the plurality of support plates are mounted. The flexible sheet is positioned at the treatment site and flexibly conforms to a surface within the patient's body, so that the light emitted by the plurality of light sources is directed into tissue at the treatment site. Further included are a plurality of flexible leads that are coupled to the plurality of electrical conductors on the plurality of support plates and are adapted to convey electrical current to the plurality of electrical conductors. A biocompatible envelope encloses the flexible sheet and the plurality of support plates mounted thereon. At least a portion of the envelope that is adjacent to and overlies the plurality of light sources mounted on the plurality of support plates is transparent. In a preferred form of the invention, some of the plurality of light sources are activated at one time, and others are activated at a different time, to minimize heating of tissue at the treatment site.

In one preferred form of the invention, the means for directing comprise a plurality of lenses. Each of the plurality of light sources includes one of the plurality of lenses, and the plurality of lenses focus light emitted by the plurality of light sources in desired directions. In an alternative embodiment, the means for directing comprise a plurality of mirrors. Each of the plurality of light sources includes one of the plurality of mirrors, and the plurality of mirrors focus light emitted by the plurality of light sources in desired directions.

The plurality of light sources are preferably arranged in a spaced-apart array on one surface of the support plate. As a further alternative, the means for directing the plurality of light sources comprise inclined mounting bases that orient the plurality of light sources at different angles relative to the support plate. Preferably, the plurality of light sources comprise either light emitting diodes or laser diodes.

One of the advantages of the present invention is that it can be used to destroy microscopic, diffuse metastatic cells within an organ disposed internally within the patient's body. The long wavelength light emitted by the plurality of light sources penetrate deep within the internal organ reaching metastatic cells that are substantially below a surface of the organ.

Another advantage is that the location of the support plate and light source array on the organ surface obviates the need for breaching the organ parenchyma. The superficial location greatly reduces the risk of bleeding and fistula formation, which is inherent to an intraparynchymal device.

A further aspect of the present invention is directed to a method for administering a photodynamic therapy to a treatment site within an internal organ of a patient's body using light in an infrared or near infrared waveband. The photodynamic therapy destroys microscopic, diffuse metastatic cells in the internal organ that have absorbed a photoreactive agent having a characteristic light absorption waveband substantially shorter than the near infrared waveband. This method thus includes steps that are generally consistent with the functions performed by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
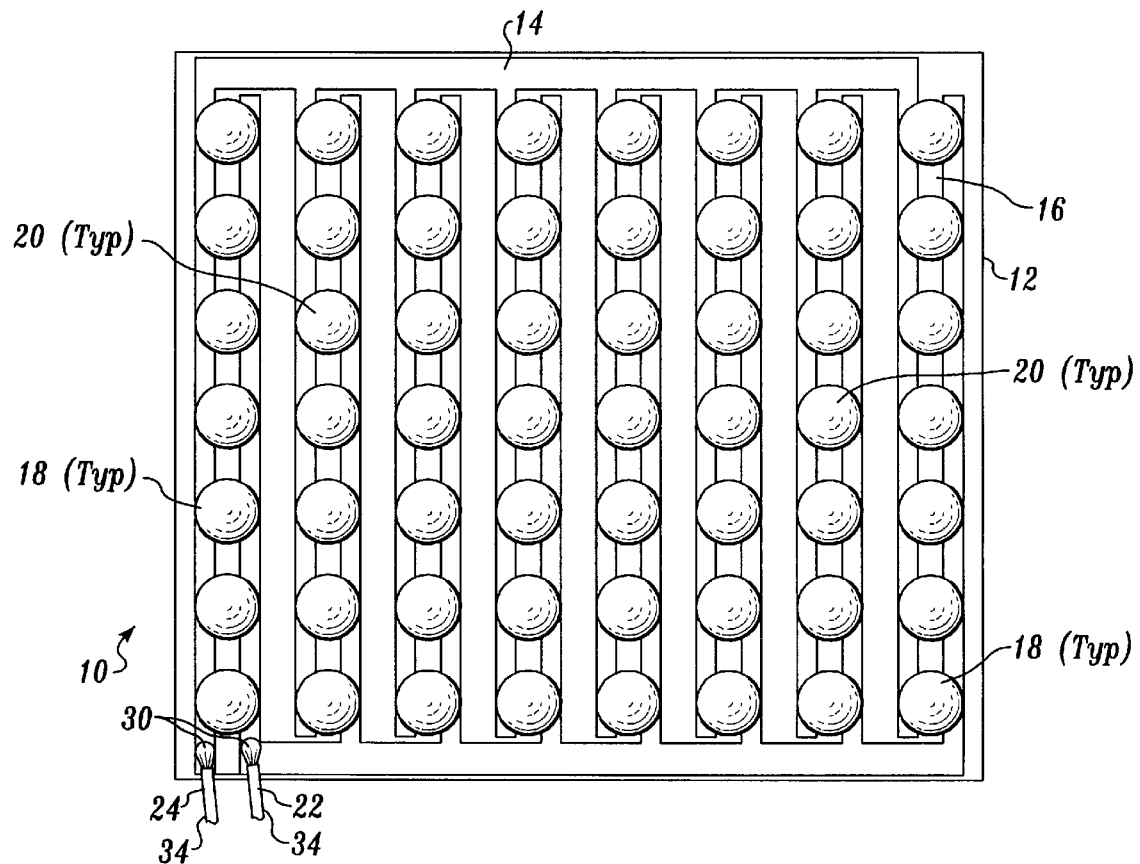
FIG. 1 is a top plan view of support plate on which are mounted a plurality of light sources that emit light having a long wavelength, in accord with the present invention.

As noted above in the Background of the Invention, the prior art teaches that the efficacy of two photon absorption by a photodynamic agent to implement PDT varies quadratically with the intensity of a laser source for the infrared waveband light that has been used for this technique in the prior art. However, the present invention takes a different approach to achieving two photon interaction that does not use such a high intensity light source. Instead of using a single focused high intensity laser light source, as in the prior art, the present invention uses a plurality of light sources, generally as shown in FIG. 1. These light sources are preferably light emitting diodes (LEDs) or laser diodes configured as an array 10, including light sources 18 around the periphery of the array, and light sources 20 in the interior of the array. Light sources 18 and 20 emit light having a characteristic long wavelength that is in the infrared waveband. It is also contemplated that light sources can be selected, which emit light in the near infrared waveband. However, longer wavelength light is preferable, since as noted in the above discussion of the prior art Ti:sapphire laser, the longer wavelength light penetrates much more deeply into tissue at a treatment site than short wavelength light.

Array 10 includes a support plate 12 formed of a suitable electrically insulating polymer, which is relatively rigid. Although FIG. 1 shows a support plate that is square, it will be understood that support plate 12 can be rectangular, or may be non-quadrilateral in shape. A plurality of parallel conductive traces 14 are applied to the upper surface of support plate 12 and are interleaved with a corresponding plurality of conductive traces 16, forming pairs of spaced-apart conductive traces 14 and 16 on which the plurality of light sources are mounted. In the preferred embodiment illustrated, light sources 18 differ from light sources 20 only in the directions in which light emitted thereby is directed.

Specifically, light sources 18 all direct the light they emit in various directions that are slightly angled toward the interior of array 10. In contrast, light sources 20 direct the light emitted thereby in a plurality of different directions, all of which are generally oriented away from support plate 12. By varying the angle at which the light emitted by the light sources is directed, the likelihood that the light emitted by one light source will intersect the light emitted by another light source is increased, thereby increasing the probability of two photon absorption by a photoreactive agent infused into the treatment site toward which the light is directed. Further discussion of this point is set forth below.

The light sources in array 10 are energized by an electrical current applied to conductive traces 14 and 16 through leads 22 and 24. Leads 22 and 24 are connected to conductive traces 14 and 16 by drops of solder 30. Alternatively, drops of conductive adhesive can be used to attach leads 22 and 24 to the conductive traces. Except where connected to the conductive traces, leads 22 and 24 are enclosed by an electrically insulating polymeric layer 34 of the type commonly used for insulated electrical leads.

Figure 2:
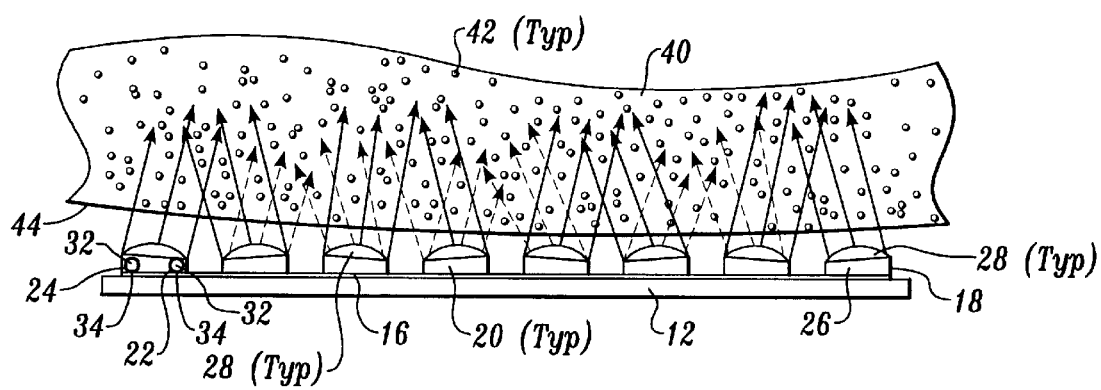
FIG. 2 is a side elevational view of the support plate, showing a front row of the plurality of light sources emitting light along intersecting paths.

As illustrated in FIG. 2, the long wavelength light emitted by light sources 18 and 20 penetrates deeply within a treatment site 40. Prior to administering long wavelength light to the treatment site, it is infused with an appropriate photoreactive agent, such as psoralen. Other suitable photoreactive agents having a characteristic absorption waveband that is much shorter than that of the light emitted by light sources 18 and 20 can alternatively be used. A plurality of microscopic, diffuse metastatic cancerous cells 42 randomly distributed throughout the tissue at treatment site 40 preferably absorb the psoralen or other photoreactive agent that has been infused into the treatment site. The long wavelength light emitted by light sources 18 and 20 penetrates deeply into the tissue of the treatment site so that photons comprising the light rays interact with metastatic cancer cells 42, causing a two photon absorption to occur.

Although a photoreactive agent infused into the treatment site, such as psoralen, has a characteristic light absorption waveband in the ultraviolet range, two photon absorption of light in the infrared or near infrared waveband can nevertheless cause a photodynamic reaction. Thus, when two photons of the long wavelength light impact a metastatic cancer cell that has absorbed the photoreactive agent, the agent is activated by the two photons, causing the same therapeutic result as if light in the characteristic absorption waveband of the agent (i.e., in the ultraviolet waveband) had been absorbed by the material. The resulting photodynamic reaction destroys the metastatic cancer cell. Since these metastatic cancer cells are diffusely distributed throughout treatment site 40, and because the light emitted by the light sources is not nearly as intense as that produced by the Ti:sapphire laser of the prior art, the PDT therapy must be administered for substantially longer time to have the expected therapeutic result. In other words, although two photon absorption by the photoreactive agent occurs much less often than would be the case if a much higher intensity laser light source were used, the longer duration of the treatment enables the same therapeutic result. Furthermore, since the light rays emitted by the light sources on array 10 are not focused at a particular point, but instead are directed at various angles throughout treatment site 40, two photons comprising different rays are more likely to intersect diffusely distributed metastatic cancer cells 42 in a manner that is not possible with a focused high intensity laser light source, like that disclosed in the prior art.

Figure 3:
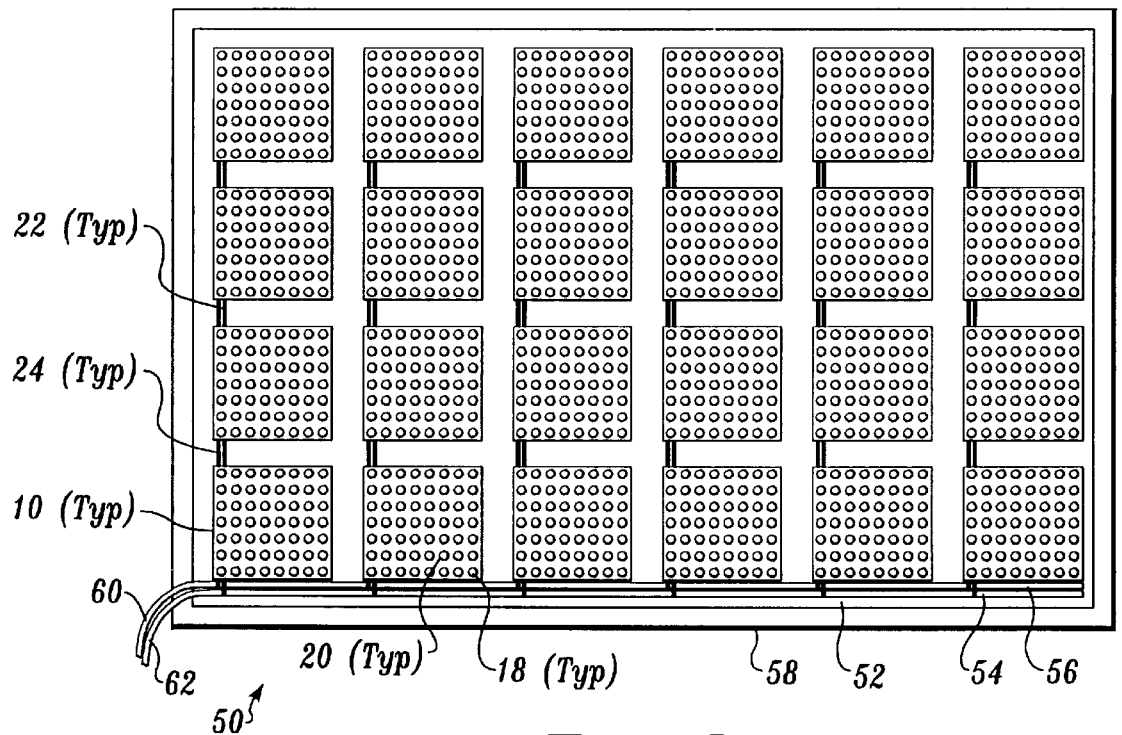
FIG. 3 is a top plan view of a plurality of the support plates mounted on a flexible sheet and enclosed within a biocompatible, transparent envelope.
Figure 4:
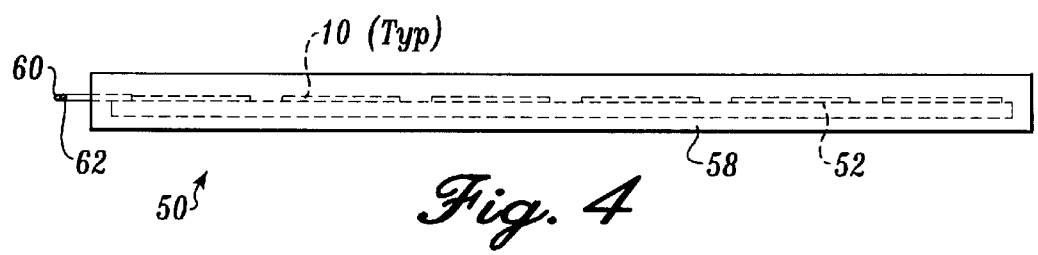
FIG. 4 is a side elevational view of the flexible sheet shown in FIG. 3.
Figure 5:
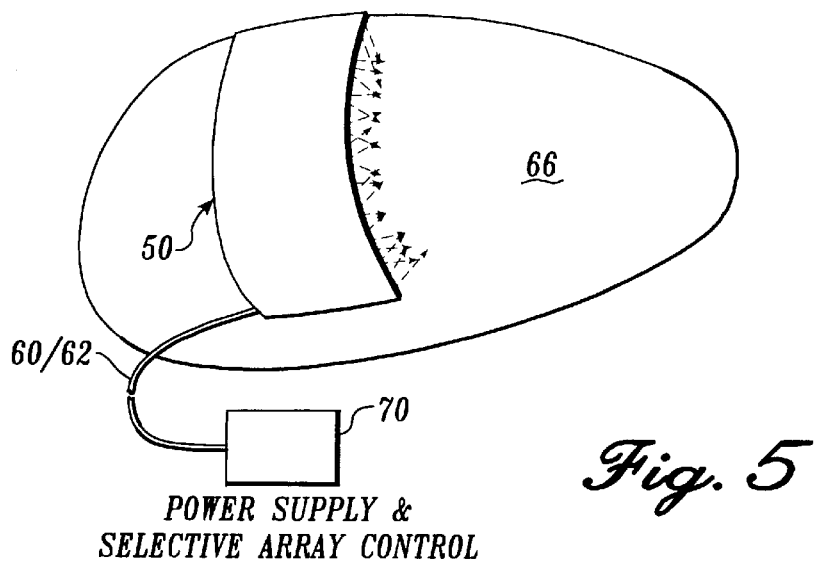
FIG. 5 is a schematic view showing how the flexible sheet is used to administer PDT to destroy metastatic cancer cells randomly dispersed within a liver inside a patient's body.

While array 10 of light sources 18 and 20 would be useful for administering two photon absorption PDT to a relatively small treatment site, the spread of metastatic cancer cells more often occurs throughout an organ having a substantially larger size than could readily be treated by array 10. To treat an organ such as a liver 66, as shown in FIG. 5, a probe 50 (shown in FIGS. 3 and 4) is provided that includes a plurality of arrays 10 mounted on a flexible sheet 52. Flexible sheet 52 is fabricated from a polymer selected for its flexible characteristics i.e., its ability to be folded over without damage and undue resistance, and in the preferred embodiment shown in FIG. 3, is illustrated as having a generally rectangular shape. Arrays 10 are attached to flexible sheet 52 in spaced-apart relationship to each other and are electrically coupled in parallel through leads 24 and 22, to conductive traces 54 and 56, which extend along one edge of flexible sheet 52. Conductive traces 54 and 56 may comprise a conductive polymer or a metallic trace deposited on flexible sheet 52 and having sufficient flexibility to bend with flexible sheet 52 without damage. Because of its flexibility, the flexible sheet conforms around the exterior surface of an organ or other treatment site, such as liver 66. Furthermore, conductive traces 54 and 56 are connected through insulated leads 60 and 62 to a power supply 70, generally as shown in FIG. 5.

To protect the plurality of arrays 10 comprising probe 50 from mechanical damage and from exposure to body fluids, flexible sheet 52 and the plurality of arrays 10 mounted thereon are encapsulated within a biocompatible envelope 58 that is optically transparent. Biocompatible envelope 58 is sealed around the edges of flexible sheet 52 and around leads 60 and 62, where the leads pass through the periphery of the envelope. Biocompatible envelope 58 is fabricated from a polymer that is sufficiently flexible to bend without damage, and thus to conform to the shape of a treatment site, such as liver 66.

The long wavelength light emitted by light sources 18 and 20 on each of arrays 10, which is graphically indicated by a plurality of arrows in FIG. 5, covers a substantially larger area of the organ to which the PDT is being administered. However, it is likely that the total area covered by the arrays mounted to flexible sheet 52 may be less than that of the organ or other treatment site to which the PDT is being administered. If so, probe 50 is moved to overlie a different portion of the surface of the organ being treated, after the PDT has been administered for a duration of time sufficient so that metastatic cells are destroyed in the portion of the organ previously treated with probe 50. In this manner, the entire organ can be treated with two photon absorption PDT to destroy the diffuse metastatic cancer cells within the organ.

Because of its flexible nature, probe 50 can readily be inserted transcutaneously into a patient's body while rolled up, e.g., by insertion through a laparoscopic guide tube or using other conventional laparoscopic techniques, and the rolled or folded flexible sheet can then be maneuvered into position for administering long wavelength light to the treatment site. Once positioned adjacent the treatment site, the rolled or folded flexible sheet is unrolled or unfolded and spread over the surface of the organ or other treatment site to which the long wavelength light will be administered. If necessary to move the probe, conventional endoscopic techniques can again be applied to grasp the probe and shift it to a different position at the treatment site.

Power supply 70 is also preferably implanted inside the patient's body, at a site spaced apart from the organ or other treatment site where the probe is positioned. Although a battery will likely be included in power supply 70, the battery is preferably charged in situ using an electromagnetic receiver coil (not shown) disposed subdermally within the patient's body. The electromagnetic receiver coil is inductively coupled to an external electromagnetic coil (also not shown) that is energized by an alternating electrical current from an external source. These components and details of power supply 70 are not shown in the drawing figures, since they do not specifically relate to the present invention.

A key aspect of the present invention is its ability to direct the long wavelength light emitted by the plurality of light sources along paths into the tissue so that the light emitted by different light sources intersect, thereby increasing the likelihood of two photon absorption. In connection with this object, FIG. 2 illustrates how light sources 20 are mounted on angled bases 26 at different angles and include convex lenses 28 to insure that the light emitted by each light source travels in a desired direction, generally with minimal spherical dispersion. As also shown in FIG. 2, the direction in which light emitted by adjacent light sources is oriented is varied, to insure that the light emitted by one light source intercepts the light emitted by a different light source. In this Figure, the light emitted by light sources immediately behind those shown are indicated by dashed arrows, while the light emitted by light sources visible in the foreground of the Figure is indicated by solid arrows. It is also contemplated that bases 26 can be oriented at varying angles relative to the support plate to provide greater diversity and variation in the direction in which light emitted from the plurality of light sources is directed into tissue at the treatment site.

Figure 6:
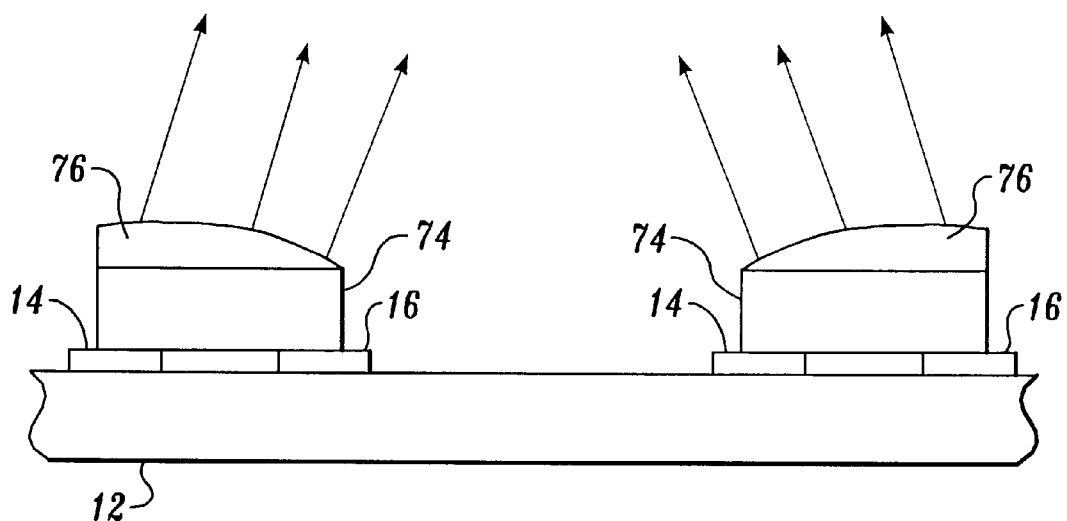
FIG. 6 is a side elevational view of two light sources, illustrating a first embodiment that uses lenses for directing light emitted by the light sources.

An alternative approach for directing light emitted by the light sources is illustrated in FIG. 6. In this embodiment, light sources 74 each include an asymmetric convex (or wedge shaped) lens 76 that directs the light emitted by the light source at an acute angle, relative to the central axis of the light source, so that the light emitted by the light sources is directed in a plurality of different directions, relative to support plate 12. Again, varying shapes for asymmetric convex (or wedge shaped) lenses 76 can be employed to provide greater diversity in the directions in which light emitted from each light source is directed.

Figure 7:
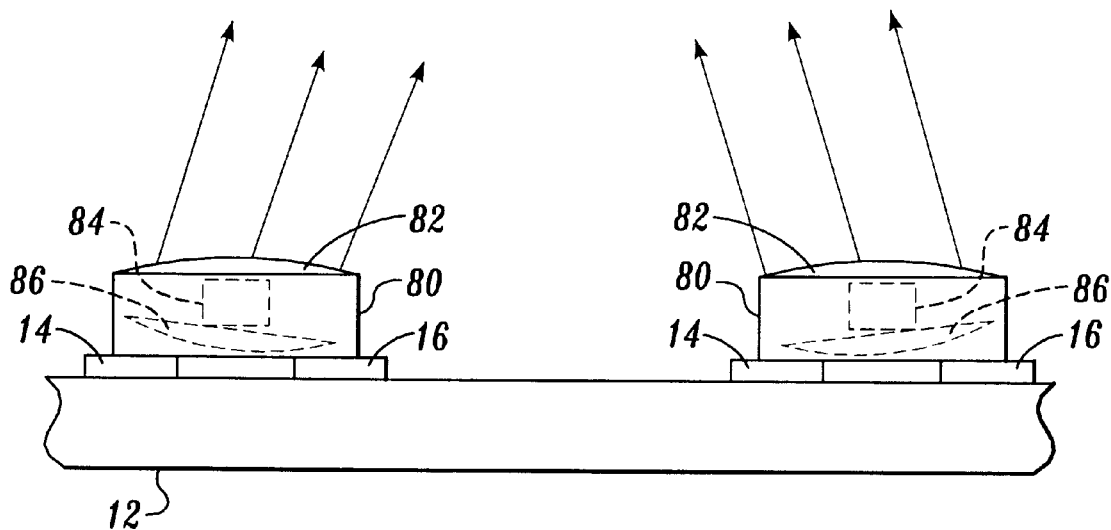
FIG. 7 is a side elevational view of two light sources, illustrating a second embodiment that uses mirrors for directing light emitted by the light sources.

In FIG. 7, yet another alternative embodiment is illustrated for directing the light emitted by each light source in different directions. A light source 80 includes a light emitting diode or laser diode 84 mounted in a cavity, above a convex mirror 86 that is angled to reflect light emitted from the solid state source in a desired direction. By varying the relative orientation or position of convex mirrors 86 within the cavity, it is thus possible to ensure that the light emitted from each such light source is likely to cross the light emitted by a different source within the tissue of the treatment site.

Since the plurality of light sources used in the present invention may heat the tissue to an excessive temperature that might damage healthy tissue at the treatment site, it is contemplated that it may be desirable to energize only a portion of the light sources on probe 50 at one time, with another portion being subsequently energized. For example, the light sources in every other array 10 mounted on flexible sheet 52 (as in a checkerboard pattern) can be selectively energized for an interval of time, e.g., ten minutes, and then de-energized while the previously de-energized light sources in the other arrays 10 are then energized. The localized heating caused by the light sources will then be minimized, since the tissue adjacent each array 10 will have an opportunity to cool between the times that the array of light sources is energized. Further, the benefit of this technique will be to extend the intervals at which the battery in power supply 70 needs to be recharged using the external inductively coupled power source noted above.

Although the present invention has been described in connection with the preferred form of practicing it, those of ordinary skill in the art will understand that many modifications can be made thereto within the scope of the claims that follow. Accordingly, it is not intended that the scope of the invention in any way limited by the above description, but instead be determined entirely by reference to the claims that follow.

The invention in which an exclusive right is claimed is defined by the following:

1. Apparatus for administering a photodynamic therapy to a treatment site within a patient's body using light having an infrared or near infrared waveband for destroying microscopic, diffuse metastatic cells at the treatment site that have absorbed a photoreactive agent having a characteristic absorption waveband for light that is substantially shorter than the near infrared waveband, comprising:

(a) a support plate on which are disposed a plurality of electrical conductors that are adapted to couple to a source of an electrical current;

(b) a plurality of light sources mounted on the support plate, in electrical contact with the plurality of electrical conductors so that the plurality of light sources are energized by an electrical current conveyed by the plurality of electrical conductors, said light sources emitting the light having a long wavelength that is in the near infrared to infrared waveband; and (c) means for directing the light emitted by the plurality of light sources so that the light emitted from one light source crosses the light emitted by a different light source, thereby increasing a likelihood of two photons substantially simultaneously being absorbed by the photoreactive agent in a microscopic, diffuse metastatic cell at the treatment site, to destroy said cell by a photodynamic reaction.

2. The apparatus of claim 1, further comprising:

(a) a plurality of support plates, each including a plurality of light sources mounted thereon that are energized by current conveyed by a plurality of conductive traces; and (b) a flexible sheet on which the plurality of support plates are mounted, said flexible sheet being positioned at the treatment site and flexibly conforming to a surface thereof so that the light emitted by the plurality of light sources is directed into tissue at the treatment site.

3. The apparatus of claim 2, further comprising a plurality of flexible leads that are coupled to the plurality of electrical conductors on the plurality of support plates and are adapted to convey electrical current to the plurality of electrical conductors.

4. The apparatus of claim 2, further comprising a biocompatible envelope that encloses the flexible sheet and the plurality of support plates mounted thereon, said envelope being transparent at least in a portion thereof that is adjacent to and overlies the plurality of light sources mounted on the plurality of support plates.

5. The apparatus of claim 2, wherein a portion of the plurality of light sources are activated at one time and a different portion at a different time, to minimize heating of tissue at the treatment site.

6. The apparatus of claim 1, wherein the means for directing comprise a plurality of lenses, each of the plurality of light sources including one of the plurality of lenses, said plurality of lenses focusing light emitted by the plurality of light sources in different directions.

7. The apparatus of claim 1, wherein the means for directing comprise a plurality of mirrors, each of the plurality of light sources including one of the plurality of mirrors, said plurality of mirrors focusing light emitted by the plurality of light sources in different directions.

8. The apparatus of claim 1, wherein the plurality of light sources are arranged in a spaced-apart array on one surface of the support plate.

9. The apparatus of claim 1, wherein the means for directing comprise inclined mounting bases for the plurality of light sources that orient the plurality of light sources at a plurality of different angles relative to the support plate.

10. The apparatus of claim 1, wherein the plurality of light sources are selected from one of light emitting diodes and laser diodes.

11. The apparatus of claim 1, wherein the treatment site is an organ disposed internally within the patient's body.

12. A method for administering a photodynamic therapy to a treatment site within an internal organ of a patient's body using light having an infrared or near infrared waveband, for destroying microscopic, diffuse metastatic cells in the internal organ that have absorbed a photoreactive agent having a characteristic light absorption waveband substantially shorter than the near infrared waveband, comprising the steps of:

(a) administering the photoreactive agent to the patient, said photoreactive agent being selectively preferentially absorbed by the microscopic, diffuse metastatic cells in the organ, at the treatment site;

(b) positioning a plurality of light sources at the treatment site, said plurality of light sources emitting light in the infrared or near infrared waveband;

(c) directing the plurality of light sources toward an interior of the organ, so that light emitted thereby travels along different crossing paths; and (d) energizing the plurality of light sources to emit the light in the near infrared or infrared waveband, said light penetrating the organ to at least a predetermined depth, causing two photon absorption by the microscopic, diffuse metastatic cells in the organ, thereby destroying said cells.

13. The method of claim 12, wherein the step of directing comprises the step of mounting the plurality of light sources so that they are oriented in a plurality of different directions.

14. The method of claim 12, wherein the step of directing comprises the step of providing the plurality of light sources with a plurality of lenses that focus the light emitted from the plurality of light sources in different directions.

15. The method of claim 12, wherein the step of directing comprises the step of providing the plurality of light sources with a plurality of mirrors that focus the light emitted from the plurality of light sources in different directions.

16. The method of claim 12, wherein the plurality of light sources are mounted on a plurality of support plates attached to a flexible sheet.

17. The method of claim 16, wherein the step of positioning comprises the step of conforming the flexible sheet around an outer surface of the internal organ, with the plurality of light sources directed to emit light into an interior of the internal organ.

18. The method of claim 12, further comprising the step of energizing the light sources with short duration pulses of an electrical current to increase the intensity of the light emitted thereby, while maintaining a substantially lower average electrical current.

19. The method of claim 12, wherein the plurality of light sources are selected from one of light emitting diodes and laser diodes.

20. The method of claim 12, wherein the light sources are arranged on a plurality of support plates in a spaced-apart array.

21. The method of claim 12, wherein different portions of the plurality of light sources are sequentially energized to emit the light, thereby reducing the energy required and minimizing heating of the internal organ.

22. The method of claim 12, further comprising the step of protecting the plurality of light sources in a sealed biocompatible envelope that encloses the plurality of light sources, at least a portion of the envelope overlying the plurality of light sources being substantially optically transparent.

23. The method of claim 12, wherein the plurality of light sources are energized while the patient is ambulatory, said plurality of light sources being energized over an extended period of time to destroy the microscopic, diffuse metastatic cells.

24. The method of claim 12, further comprising the step of repositioning the plurality of light sources to administer light to a different portion of the internal organ.

* * * * *